US006799064B1

(12) United States Patent
Hassett

(10) Patent No.: US 6,799,064 B1
(45) Date of Patent: Sep. 28, 2004

(54) DEVICE FOR THE MAPPING OF CARDIAC ARRHYTHMIA FOCI

(75) Inventor: James A. Hassett, Bloomington, MN (US)

(73) Assignee: St. Jude Medical, Daig division, Minnetonka, MN (US)

(*) Notice: Subject to any disclaimer, the term of this patent is extended or adjusted under 35 U.S.C. 154(b) by 105 days.

(21) Appl. No.: 10/224,067

(22) Filed: Aug. 20, 2002

Related U.S. Application Data

(63) Continuation-in-part of application No. 09/570,279, filed on May 12, 2000, now Pat. No. 6,466,811.
(60) Provisional application No. 60/133,984, filed on May 13, 1999.

(51) Int. Cl.[7] ................................................ A61B 5/04
(52) U.S. Cl. ........................ 600/374; 600/381; 607/122
(58) Field of Search .............................. 600/373–375, 600/377, 381; 607/119, 122

(56) References Cited

U.S. PATENT DOCUMENTS

| | | |
|---|---|---|
| 4,332,259 A | 6/1982 | McCorkle, Jr. |
| 4,365,639 A | 12/1982 | Goldreyer |
| 4,641,649 A | 2/1987 | Walinsky et al. |
| 4,649,924 A | 3/1987 | Taccardi |
| 4,660,571 A | 4/1987 | Hess et al. |
| 4,945,912 A | 8/1990 | Langberg |
| 5,127,403 A | 7/1992 | Brownlee |
| 5,156,151 A | 10/1992 | Imran |
| 5,172,694 A | 12/1992 | Flammang et al. |
| 5,174,288 A | 12/1992 | Bardy |
| 5,215,103 A | 6/1993 | Desai |
| 5,228,442 A | 7/1993 | Imran |
| 5,231,995 A | 8/1993 | Desai |
| 5,239,999 A | 8/1993 | Imran |

(List continued on next page.)

FOREIGN PATENT DOCUMENTS

| | | |
|---|---|---|
| CA | 1192263 | 8/1985 |
| EP | 0373953 | 6/1990 |
| WO | WO92/21285 | 12/1992 |

OTHER PUBLICATIONS

K.L. Drake, et al., "Performance of Planar Multisite Microprobes in Recording Extracellular Single–Unit Intracortical Activity", IEEE Transactions on Biomedical Engineering, vol. 35, No. 9, Sep. 1988, pp 719–732.
Tracy, C.M. "Radio Frequencey Catheter Ablation of Ectopic Atrial Tachycardia Using Paced Activation Sequence Mapping" J. AM. Coll. Cardiol. vol. 21. pp. 910–917 (1993).
Walsh, Edward P. "Ablation of Ectopic Atrial Tachycardia in Children". Radio Frequency Catheter Ablation of Cardiac Arrhythmias, Chap. 23 (1994).
Jackman, Warren M. "New Catheter Technique for Recording Left Free–Wall Accessory Atroventricular Pathway Activation" American Heart Association Circ., vol. 78, No. 3, Part 1, Sep. 1998, pp 598–611.

*Primary Examiner*—Lee S. Cohen
(74) *Attorney, Agent, or Firm*—Scott R. Cox

(57) ABSTRACT

A device for the mapping of cardiac arrhythmia foci including a catheter body having a distal end, first and second point electrodes, which are secured in the surface of the catheter body and which form a first bipolar pair of electrodes, and third and fourth point electrodes, which are secured in the surface of the catheter body and which form a second bipolar pair of electrodes, wherein a line passing between the third and fourth point electrodes is within about 45 degrees of being perpendicular to a line passing through the first and second point electrodes and wherein all four point electrodes are secured to that portion of the surface of the catheter body forming no more than half of the circumference of the surface of the catheter body when viewed from the distal tip of the catheter so that all four electrodes can be in contact with the cardiac tissue at the same time during a cardiac procedure.

23 Claims, 2 Drawing Sheets

U.S. PATENT DOCUMENTS

| | | |
|---|---|---|
| 5,263,493 A | 11/1993 | Avitall |
| 5,281,217 A | 1/1994 | Edwards et al. |
| 5,385,146 A | 1/1995 | Goldreyer |
| 5,391,194 A | 2/1995 | Goldreyer |
| 5,398,683 A | 3/1995 | Edwards et al. |
| 5,423,772 A | 6/1995 | Lurie et al. |
| 5,450,846 A | 9/1995 | Goldreyer |
| 5,476,499 A | 12/1995 | Hirschberg |
| 5,579,764 A | 12/1996 | Goldreyer |
| 5,755,761 A | 5/1998 | Obino |
| 5,824,030 A | 10/1998 | Yang et al. |
| 5,921,923 A | 7/1999 | Kuck et al. |
| 6,093,157 A | 7/2000 | Chandrasekaran |
| 6,466,811 B1 | 10/2002 | Hassett |
| 6,498,943 B2 * | 12/2002 | Steglich ............... 600/374 |
| 6,673,068 B1 * | 1/2004 | Berube ............... 600/374 |

* cited by examiner

DEVICE FOR THE MAPPING OF CARDIAC ARRHYTHMIA FOCI

CROSS REFERENCE TO RELATED APPLICATIONS

This application is a continuation-in-part of application Ser. No. 09/570,279, filed May 12, 2000, now U.S. Pat. No. 6,466,811, which application claims the benefit of U.S. Provisional Application No. 60/133,984, filed May 13, 1999.

BACKGROUND OF INVENTION

1. Field of Invention

This invention relates to a device for the mapping of cardiac arrhythmia foci. In particular, it relates to a catheter which is useful for the mapping of cardiac arrhythmia foci containing a grouping of small, non-ring shaped, point electrodes preferably formed in a diamond-shaped configuration, which when activated, produce a pair of bipoles on the catheter.

2. Prior Art

Catheters have been in use for medical procedures for many years. For example, one use is to convey an electrical stimulus to a selected location within the human body. Another use is to assist in monitoring and measuring electrophysiological activity for diagnostic tests within the human body. Thus, catheters may assist in examination, diagnosis and treatment within a human body while positioned at a specific location, which is otherwise inaccessible without more invasive procedures. In use, catheters are inserted into a vein or artery which is near the body surface. These catheters are then guided to a specific location for examination, diagnosis or treatment by manipulating the catheter through the artery or vein of the human body.

Catheters have become increasingly useful in remote and difficult to reach locations within the body. Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

Cardiac arrhythmia may be transient or persistent. While most arrhythmia occur in individuals having other forms of underlying heart disease, some arrhythmia occur independently. While atrial arrhythmia do not directly cause death as frequently as ventricular arrhythmia, they increase the risk factor for a number of other diseases such as strokes, thrombosis, atherosclerosis, systemic and cerebral embolism and cause a number of additional medical problems. Atrial fibrillation is the most common sustained heart arrhythmia. It is estimated to occur in upwards of 0.4 percent of the adult population and perhaps as many as 10 percent of the population who are 60 years or older.

Certain patients with symptomatic or life threatening cardiac arrhythmia cannot be adequately treated by drugs or common medical devices, such as defibrillation, or by cardioversion. Other forms of treatment are then mandated, which may include surgery.

Another procedure used for treatment of certain types of cardiac arrhythmia within the last 10 to 15 years is catheter ablation. This procedure has been used to interrupt or modify existing conduction pathways associated with arrhythmias within the heart. The particular area for ablation depends on the type of underlying arrhythmia. One common ablation procedure treats atrioventricular (AV) nodal reentrant tachycardia. With this problem ablation of the fast or slow AV nodal pathways has become an accepted treatment. The use of ablation catheters for ablating locations within the heart has been disclosed, for example in U.S. Pat. Nos. 4,641,649, 5,263,493, 5,231,995, 5,228,442 and 5,281,217.

In addition, catheter ablation for the treatment of ectopic atrial tachycardia is disclosed, for example, in Walsh, Edward P. "Ablation of Ectopic Atrial Tachycardia in Children" *Radio Frequency Catheter Ablation of Cardiac Arrhythmias*, Chap. 23 (1994). See also Tracey, C. N. "Radio Frequency Catheter Ablation of Ectopic Atrial Tachycardia Using Paced Activation Sequence Mapping" J. Am. Coll. Cardial. Vol 21, pp. 910–917 (1993).

The sources of energy used for catheter ablation vary. Initially, high voltage, direct current (D.C.) ablation techniques were commonly used. However, because of problems associated with the use of D.C. current, radio frequency (RF) ablation has become a preferred source of energy for the ablation procedures. Other energy sources also considered for ablation of heart tissue include laser, ultrasound, microwave and fulgutronization.

Ablation of a precise location within the heart, such as a focus of a cardiac arrhythmia, requires the precise placement of the ablation catheter within the heart. Precisely positioning the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

Accordingly, the treatment of cardiac arrhythmia has increasingly been dependent upon the ability to identify the precise location or origin in the heart of the abnormal rhythm. The prior art practice for locating an abnormal rhythm is to place a catheter within the heart carrying a standard array of ring and/or tip electrodes. Direct contact of the tip electrode with the cardiac tissue is used for making an intracardiac electrogram in a manner similar to that has been practiced for many years with respect to pacemaker sensing. See, for example, U.S. Pat. Nos. 5,156,151 and 4,365,639.

A relatively new process for sensing arrhythmia within a heart utilizes one or more pairs of circumferential, orthogonal sensing electrodes, such as are disclosed in U.S. Pat. No. 4,365,639. See also Canadian Patent No. 1,192,263. A series of circumferential orthogonal electrodes located in pairs around the body of a catheter are disclosed in U.S. Pat. Nos. 5,385,146, 5,450,846 and 5,579,764. These patents disclose a process whereby a pair or a series of pairs of circumferential orthogonal electrodes are used in conjunction with an ablation or pacing catheter simultaneously to sense electrophysiological activity in the heart and to pace or ablate predetermined locations in the heart. Only localized cardiac signals at precise locations within the cardiac tissue of the heart immediately adjacent to the predetermined location where the orthogonal electrodes are positioned are sensed by the orthogonal electrode pairs. The specific design and arrangement of these orthogonal electrode pairs limits their use within the heart to simultaneous sensing and pacing or ablating activities. While the procedures disclosed by these patents are quite useful once the focus of the cardiac arrhythmia has been determined, it is necessary to first identify the general location of the arrhythmia focus within the cardiac tissue.

Accordingly, it is an object of the invention to disclose a product for the mapping of cardiac tissue to disclose the location of cardiac arrhythmia foci.

It is a further object of the invention to disclose a catheter containing a plurality of point electrodes which form a pair of bipoles for the sensing of the direction of an activation wave generated by cardiac arrhythmia foci as the wave passes the pair of bipoles.

It is a still further object of the invention to disclose a catheter for the sensing of the direction of an activation wave generated by cardiac arrhythmia foci in the heart as the wave passes a pair of bipoles secured to the catheter, wherein the bipoles are formed from two pair of point electrodes formed in a diamond-shaped configuration, wherein the two pair of point electrodes are secured to the surface of the catheter within an arc of no more than 180° around the circumference of the catheter when viewed from the distal end of the catheter such that the point electrodes may be in constant contact with the surface of the cardiac tissue.

It is a still further object of the invention to disclose a catheter containing a plurality of point electrodes formed in a pattern which is capable of sensing an activation wave from an ectopic atrial tachycardia and other forms of cardiac arrhythmia foci within the heart.

It is a still further object of the invention to disclose a process for the mapping of cardiac arrhythmia foci in a heart by use of a catheter containing a plurality of point electrodes forming at least two bipoles, wherein the bipoles are preferably about 90 degrees apart from each other.

These and other objects can be obtained by the disclosed process for the treatment of cardiac arrhythmia focus and design of a catheter containing a pair of bipoles for use for that process which are disclosed by the instant invention.

SUMMARY OF INVENTION

The present invention is a catheter for sensing electrophysiological activity within a human heart comprising:

an elongated catheter body having a distal end, a first and second point electrodes which are secured to the elongated catheter body comprising a first bipolar pair of electrodes, and third and fourth point electrodes which are secured to the catheter body comprising a second bipolar pair of electrodes, wherein a line passing between the third and fourth point electrodes is within about 45 degrees of being perpendicular to a line passing through the first and second point electrodes and wherein all four point electrodes are located within the surface of the catheter forming no more than half of the circumference of the catheter when viewed from its distal end such that all four point electrodes can be in simultaneous contact with the surface of the heart during the sensing procedure.

Preferably, these four point electrodes are formed in a diamond-shaped configuration.

The present invention also includes a catheter for sensing electrophysiological activity within a human heart comprising an elongated catheter body having a distal end, a first and second point electrode which are secured to the elongated catheter body, comprising a first bipolar pair of electrodes, third and fourth point electrodes which are secured to the catheter body comprising a second bipolar pair of electrodes, wherein a line passing between the third and fourth point electrodes is within about 45 degrees of being perpendicular to a line passing through the first and second point electrodes, and wherein all four point electrodes are located within the surface of the catheter forming no more than half of the circumference of the catheter when viewed from its distal end, such that all four point electrodes are capable of simultaneous contact with the surface of the heart during the sensing procedure, and a unipolar electrode secured to the distal end of the catheter body.

Preferably, these four point electrodes are formed in a diamond-shaped configuration.

The present invention also includes a catheter for sensing electrophysiological activity within a human heart comprising an elongated catheter body having a distal end, a first and second point electrode which are secured to the elongated catheter body, comprising a first bipolar pair of electrodes, and a third point electrode which is secured to the catheter body which operates with the second point electrode to form a second bipolar pair of electrodes, wherein a line passing between the first and second point electrodes is generally perpendicular to a line passing between the second and third point electrodes and wherein all three point electrodes are located within the surface of the catheter forming no more than half of the circumference of the catheter when viewed from its distal end, such that all three point electrodes are capable of simultaneous contact with the surface of the heart during the sensing activity.

The present invention also includes a process for the mapping of cardiac arrhythmia focus activity within a heart comprising introducing a catheter within a chamber of the heart, wherein the catheter comprises an elongated catheter body having a distal end, first and second point electrodes which are secured to the elongated catheter body and which comprise a first bipolar pair of electrodes, and third and fourth point electrodes which are secured to the catheter body comprising a second bipolar pair of electrodes, wherein a line passing between the third and fourth point electrodes is within about 45 degrees of being perpendicular to a line passing through the first and second point electrodes and wherein all four point electrodes are located within the surface of the catheter forming no more than half of the circumference of the catheter when viewed from its distal end, such that all four point electrodes are capable of simultaneous contact with the surface of the heart during the mapping activity, sensing signals in heart tissue using the first and second bipolar pairs of electrodes to determine the general location of the cardiac arrhythmia focus within the heart, and determining the precise location of the cardiac arrhythmia focus using a unipole electrode secured to the catheter body.

DETAILED DESCRIPTION OF THE PREFERRED EMBODIMENT

Figure 1:
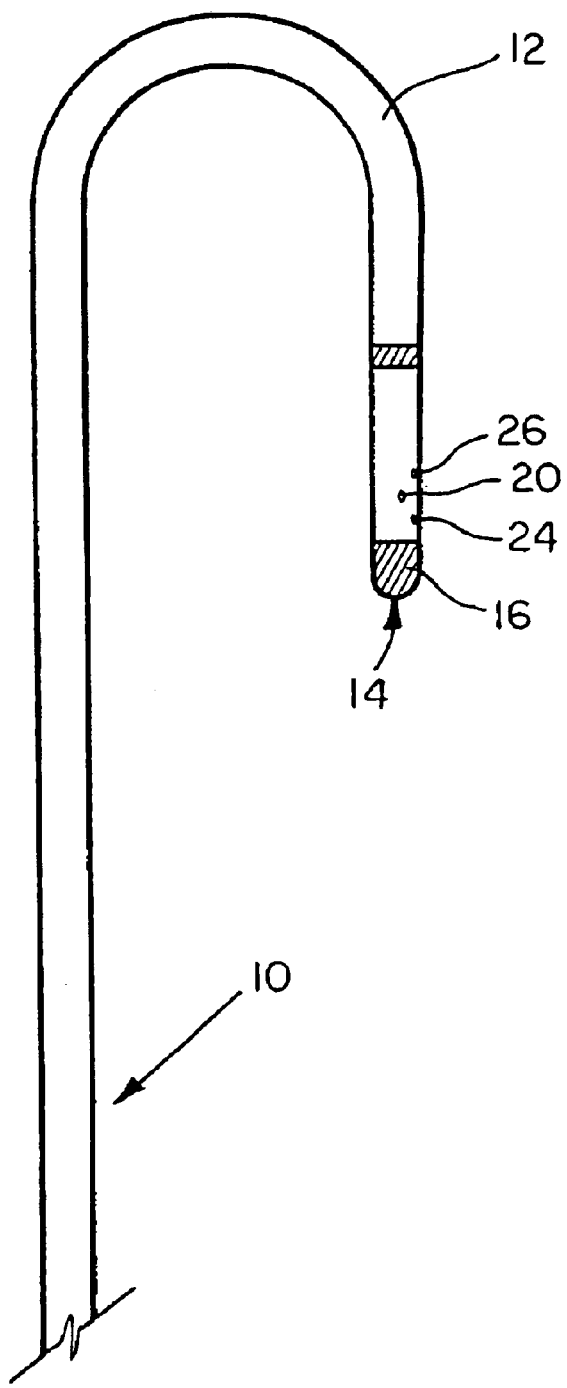
FIG. 1 is a side view of the catheter of the invention showing the point electrodes from the side of the catheter.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a thin walled, recessed portion, the fossa ovalis. Between the fossa ovalis and the tricuspid valve is the opening or ostium for the coronary sinus. The coronary sinus is the large epicardial vein which accommodates most of the venous blood which drains from the myocardium into the right atrium.

In a normal heart, contraction and relaxation of the heart muscle (myocardium) takes place in an organized fashion as electrochemical signals pass sequentially through the myocardium from the sinoatrial (SA) node to the atrialventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. Three of the most common arrhythmia are ectopic atrial tachycardia, atrial fibrillation and atrial flutter. Abnormal rhythms sometimes originate from single points of cardiac tissue which are called cardiac foci.

One type of arrhythmia focus is ectopic atrial arrhythmia ("EAT"). EAT is a cardiac rhythm disorder that involves rapid impulse generation from a single atrial focus outside the sinoatrial node. In many circumstances EAT may occur for long periods of time, possibly leading to cardiomyopathy. Because EAT is one of the few reversible causes of cardiomyopathy, more effective treatment of EAT is sought. Radio frequency ablation for the treatment of EAT is disclosed in Walsh, Edward P., "Ablation of Ectopic Atrial Tachycardia in Children," *Radio Frequency Catheter Ablation of Cardia Arrhythmias*, Chap. 23 (1994). See also Tracey, C. N. "Radio Frequency Catheter Ablation of Ectopic Atrial Tachycardia Using Paced Activation Sequence Mapping" J. Am. Coll. Cardiol. Vol 21, pp. 210–917 (1993).

While pharmacological treatments are sometimes effective in the treatment of cardiac arrhythmia, in some circumstances drug therapy is ineffective and frequently is plagued with side effects, such as dizziness, nausea, vision problems and other difficulties.

In the last few years surgical procedures have also been utilized in the treatment of some arrhythmia. The goal of these surgical procedures parallels that of the pharmacological treatments, to relieve both the subjective symptoms of arrhythmia as well as to normalize hemodynamics by restoring regular atrial contributions to the cardiac output.

The ablation catheters used to perform the ablation procedures produce scar tissue at the selected site or location within the heart. The energy necessary to scar or ablate the tissue can be provided from a number of different sources originally direct current was utilized to provide the energy for ablation procedures. More recently the preferred choice of energy source has been radio frequency energy (R.F.). Laser, microwave, ultrasound, low and high energy direct current and fulgutronization procedures have also been utilized to perform ablation procedures. The preferred source of energy for the ablation procedures of the instant invention is R.F. energy.

Significant difficulties in performing any cardiac procedure in the heart are caused by the physiology of the heart itself when beating, especially if that beating is abnormal. The preferred procedure for the treatment of arrhythmia requires the precise positioning and contact pressure of the ablation catheter within the heart to ablate a predetermined location of the arrhythmia. Mere introduction of an ablation catheter into the heart without precise placement will not be sufficient to satisfactorily ablate the desired location.

An element in the treatment of these arrhythmia also includes sensing the location of arrhythmia foci in the heart to efficiently and accurately map the cardiac tissue. The physiology of the heart and its beating also interferes with the effectiveness of sensing catheters.

Medical practitioners often monitor the introduction of cardiac catheters and their progress through the vascular system by use of fluoroscopes. Unfortunately, fluoroscopes can not easily identify specific features in the heart, in general, and the critically important structures of the various chambers of the heart in specific, thus making placement and utilization of an ablation catheter extremely difficult. This placement is especially difficult as the beating heart is in motion, resulting in the catheter moving within the heart as blood is being pumped through the heart. The specially designed catheter of the present invention addresses and solves some of these problems by assisting in the placement of the ablation catheter for accurate ablation procedures.

Figure 2:
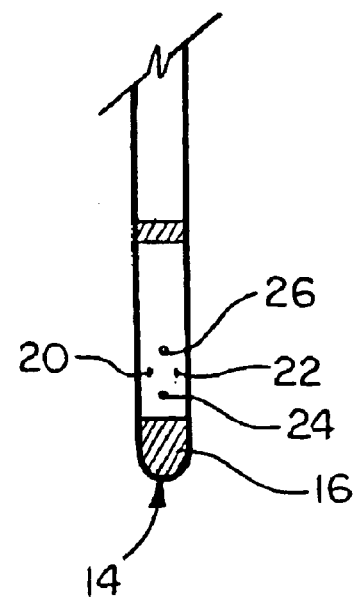
FIG. 2 is a view of the catheter of FIG. 1 rotated 90 degrees showing the four point electrodes arranged in a diamond-shaped configuration near a distal end of the catheter.

The catheter (10) of the present invention is utilized to sense electrophysiological activity within a human heart and is generally comprised of a conventional elongated catheter body (12) having a distal tip (14) as shown in FIGS. 1 and 2. The catheter body can be conventional, produced from conventional catheter materials.

Secured near the distal end of the catheter (10) is a plurality of point electrodes (20, 22, 24, 26), preferably at least two pair of these point electrodes, as shown in FIGS. 1 and 2. The first and second electrodes (20, 22) are secured to the elongated catheter body (12) and operate as a first bipolar pair of electrodes. These two point electrodes are wired conventionally to form a first bipole and are attached to a conventional sensing apparatus, such as amplifiers, to sense electrocardiac signals from throughout the heart. The bipole is operably interfaced with conventional differential receiving and processing equipment to provide directional vectors to the origin of electrophysiological activity of the heart.

These point electrodes, sometimes referred to as bead electrodes or dot electrodes, are conventional small electrodes and may be formed in any circular, rectangular, square or non-regular shape. The overall distance across the outside surface of these point electrodes is not critical as the point electrode may be any size that can be secured to a conventional electrode wire. In one preferred embodiment the size of the point electrode is at least the size of the diameter of the electrode wire secured to it, and more preferably its diameter is from about 0.1 mm. (0.004 inch) to about 2.0 mm. (0.08 inch). These point electrodes are substantially different in both size and shape from conventional tip electrodes or ring electrodes.

The first pair of point electrodes (20, 22) are located a sufficient distance apart so that they form an effective bipole. Preferably, the first pair of point electrodes are at least about 0.1 mm. (0.004 inch) apart and more preferably from about 0.1 mm. (0.004 inch) to less than about the overall diameter of the catheter body (12) apart as shown in FIGS. 2–5. However, it is important that these two point electrodes (20, 22) remain within the surface of the catheter (10) forming no more than half of the circumference of the catheter when viewed from its distal end as shown in FIG. 2. This structure permits both of these point electrodes (20, 22) to remain in constant contact with the cardiac tissue during the sensing procedure.

Figure 3:
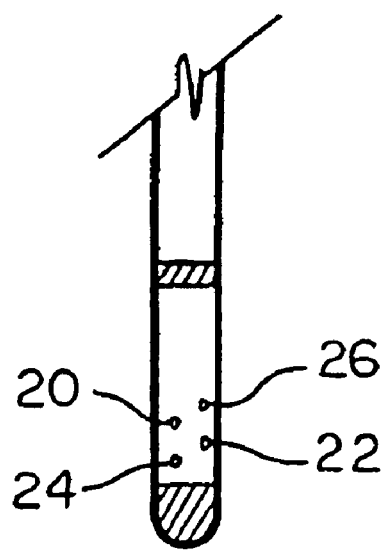
FIG. 3 is an alternative arrangement of the point electrodes near the tip of the catheter.
Figure 4:
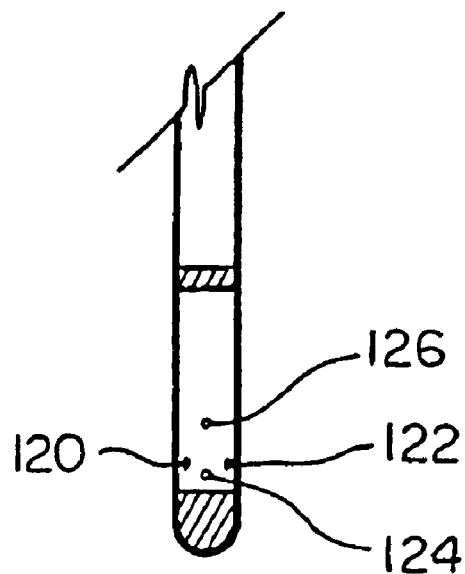
FIG. 4 is a further alternative arrangement for the point electrodes of the catheter.

The first pair of point electrodes (20, 22) may be secured to the catheter body (12) longitudinally, i.e., circumferentially located on the catheter body (12) as shown in FIG. 2, or they may be placed at various oblique angles away from a circumferential location, as shown, for example, in FIG. 3. Depending upon the diameter of the catheter body (12) and the angle that the first and second point electrodes (20, 22) form in relation to the catheter body (12), the distance between the first and second point electrodes may vary from a minimum of about 0.1 mm. (0.004 inch) to the diameter of the catheter body shaft. Typically, the largest size catheter used for this type of procedure is 12 French or 4.0 mm. (0.16 inch) in diameter, while typically the smallest catheter is 4 French or (1.3 mm.) (0.05 inch) in diameter. Thus, the distances between these first and second point electrodes may vary from a minimum of about 0.1 mm. (0.004 inch) to a maximum of about 4.0 mm. (0.16 inch) depending on the diameter of the catheter body (12).

The use of bipolar electrodes for sensing has been taught in the prior art, such as, for example, in U.S. Pat. No. 5,385,146 but only when formed as circumferential, orthogonal electrodes. The present invention discloses the use of a pair of bipole electrodes formed with particular designs which need not be circumferentially located on the catheter body and are designed not to extend 360 degrees around the surface of the catheter body. All of the electrodes are placed on the surface of the catheter on no more than half of the circumference of the catheter as shown in FIGS. 2–6.

The second pair of electrodes (24, 26) form the second bipole on the catheter. The second pair of point electrodes (24, 26) as shown in FIG. 2 are rotated away from the position of the first pair of point electrodes (20, 22). Preferably a line formed between the third and fourth point electrodes (24, 26) when compared with a line formed between the first and second electrodes (20, 22) is at least about 30 degrees apart, preferably 45 degrees and most preferably about 90 degrees apart as shown in FIG. 2. A wide variety of angles can be used for the relation between the location of the first and second bipole, each of which is within the scope of the invention. However, if an angle less than about 90 degrees is used, more complicated computations of the location of the arrhythmia being analyzed may be necessary.

It is not necessary that any of the pairs of point electrodes be longitudinally circumferential as shown, for example, in FIG. 3. However, one important aspect of the invention is that the pairs of bipoles preferably are at least about 30 degrees apart from each other and preferably 45 to 90 degrees apart as shown in FIG. 2.

It is also important that all four point electrodes (20, 22, 24, 26) are located within the surface of the catheter forming no more than half of the circumference of the catheter when viewed from its distal end as shown in FIGS. 2–6. This permits all four point electrodes (20, 22, 24, 26) to contact the cardiac tissue at the same time during the sensing procedure. Thus, all of the point electrodes (20, 22, 24, 26) are within an arc of no more than about 180 degrees around the circumference of the surface of the catheter (10).

By the placement of the point electrodes (20, 22, 24, 26) in a relatively perpendicular position, as shown in FIG. 1, the output of the bipoles can be compared electronically to determine from which general direction relative to the four electrodes the arrhythmia signal has been generated. By comparing the signals sensed by the first and second bipoles, the clinician can determine with a significant degree of specificity the direction from which the activation wave of the arrhythmia has been generated and thus determine the source of the electrical activity of the arrhythmia on the cardiac tissue. However, no specific location for the arrhythmia focus is generally possible from an initial reading of the bipoles because of variations in the time of passage and the direction of passage of the activation wave through the cardiac tissue from the arrhythmia focus.

While the bipolar pair of point electrodes (20, 22, 24, 26) as disclosed in the invention are particularly helpful in determining the general area of the arrhythmia focus on the cardiac tissue, preferably a unipolar tip electrode (16) is also secured at the distal end (14) of the catheter body (12) to operate in conjunction with at least one extracardiac electrode (not shown) to determine the precise location of the arrhythmia focus. The extracardiac electrode(s) is preferably a conventional electrode secured at a position which is significantly proximal from the most proximal of the point electrodes. Preferably the extracardiac electrode is located from about 17 cm. (6.7 inch) to about 35 cm. (13.8 inch) proximal from the most proximal of the point electrodes. Alternatively, or in addition thereto, a pair of ring electrodes may be secured to the catheter body (12) at least about 5 cm and preferably about 5 to about 20 cm apart. Conventional ring electrodes may also be secured to the catheter body at various locations to assist in the sensing procedures. For example, in one embodiment a first ring electrode is located about 2 millimeters proximal from the proximal-most point electrode. Additional ring electrodes are then located about 5 millimeter more proximal and then 2 millimeter more proximal. In addition, the tip electrode (16) secured to the distal end (14) of the catheter body (12) may function solely as a diagnostic electrode, or alternatively, it may operate as a sensing and ablation electrode.

Figure 5:
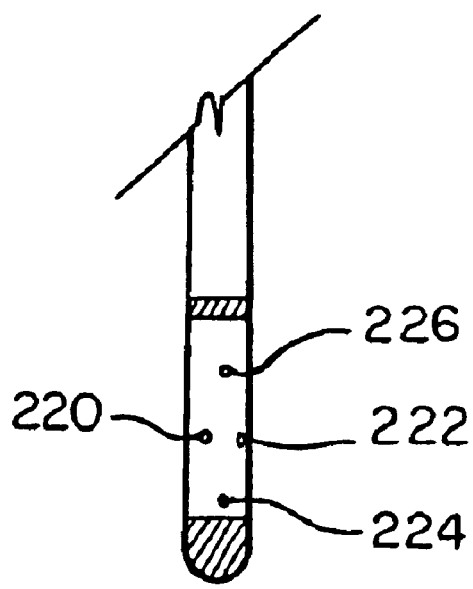
FIG. 5 is a further alternative arrangement of the point electrodes of the catheter.

The particular placement of the first bipolar pair of electrodes (20, 22) in relation to the second pair of bipolar electrodes (24, 26) can be modified as required by the user of the product. While the distance between each of the point electrodes (20, 22, 24, 26) may be approximately the same, i.e., within about 2.0 mm. (0.08 inch) and preferably from about 0.1 mm. (0.004 inch) to about 0.6 mm. (0.02 inch) apart, that distance may be varied depending upon the user of the product. It has been surprisingly discovered that an especially useful embodiment is produced when the distance between the third and fourth point electrodes (224, 226) is greater than the distance between the first and second point electrodes (220, 222), as shown in FIG. 5. In a less preferred alternative embodiment, the distal-most electrode (124) of the second bipole may be moved closer to the space between the first and second point electrodes (120, 122) as shown, for example, in FIG. 4.

Figure 6:
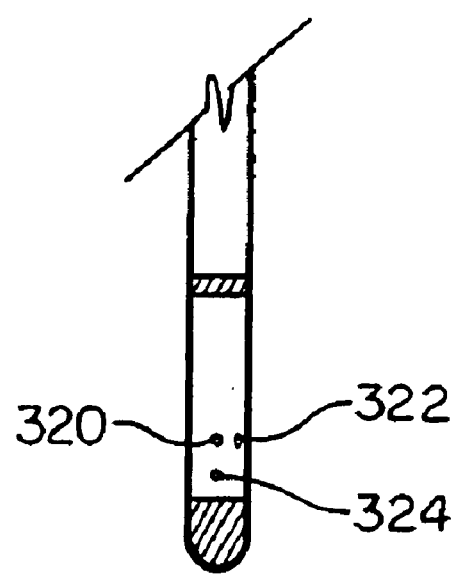
FIG. 6 is a further alternative arrangement of the point electrodes of the catheter.

In a further alternative embodiment, the first bipole is formed by placing the first and second point electrodes (320, 322) as shown in FIG. 6 in the same position as the first and second point electrodes (20, 22) as shown in FIG. 1. The second bipole is formed by a single third point electrode (324), which operates in conjunction with the first electrode (320) or the second electrode (322) to form the second bipole. In this combination, the first bipole is formed by the interaction of the first and second point electrode (320, 322) while the second bipole, for example, is formed by the interaction of the second and third point electrodes (322, 324). The angle formed by the line between the first and the second point electrodes (320, 322) and the line between the second and the third point electrodes (322, 324) may vary from about 45 degrees to about 135 degrees, preferably from about 60 to 120 degrees and most preferably around 90 degrees as shown in FIG. 6.

Processing of the signals generated by the first and second bipoles may be accomplished by conventional equipment which is well known to those skilled in the art. Based on the placement of the point electrodes on the catheter, the location of the signal from the arrhythmia focus can be generally determined. Precise location of the arrhythmia focus is difficult because the activation wave may pass through the cardiac tissue in a direct line from the arrhythmia focus point to the bipolar pair of electrodes. Once the general area of the arrhythmia focus is determined, the tip electrode (16) is activated as a unipolar electrode with an extracardiac electrode (not shown) to precisely localize the source of the arrhythmia. Once the particular location of the arrhythmia focus within the heart is determined, the tip electrode (16) may then be utilized as an ablation electrode, preferably utilizing radio frequency energy. Alternatively, a separate ablation catheter may be introduced into the heart to operate in cooperation with the catheter of the invention.

In order that the signals are sensed properly by the pair of bipolar point electrodes (20, 22, 24, 26), in a preferred embodiment the shortest distance from the conventional tip electrode (16) to the most distal point electrode (24) is at least about 3 mm. (0.12 inch) and preferably from about 3 to about 5 mm. (0.12 to 0.19 inch).

Other conventional components may be secured to the catheter body including temperature sensing devices such as thermocouples or thermistors. In addition, the catheter may be steerable using conventional steering systems.

In operation, a modified Seldinger technique is normally used for the insertion of the catheter (10) into the body. Using this procedure, a small skin incision is made at the appropriate location to facilitate the catheter (10) or dilator passage. Subcutaneous tissue is then dissected, followed by a puncture of the vessel with an appropriate needle with a stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed. The guidewire is then advanced through the vessel into the appropriate vessel. With the guidewire in place, the dilator is then placed over the guidewire with an introducer placed over the dilator. The dilator and the introducer generally form an assembly to be advanced together along the guidewire into the heart. After insertion of the assembly, the guidewire is then withdrawn.

Once the introducer is in place, the catheter (10) containing point electrodes (20, 22, 24, 26) is advanced through the introducer into the heart for the sensing procedure. The point electrodes (20, 22, 24, 26) are then placed against the surface of the cardiac tissue and are activated to sense the general direction from which the activation wave of the arrhythmia focus is generated. By locating all of the point electrodes (20, 22, 24, 26) on no more than half of the circumference of the surface of the catheter body, all four electrodes can simultaneously be in contact with the cardiac tissue during the sensing procedure. By repeating this sensing procedure within the chamber of the heart as needed, the pair of bipolar sensing electrode pairs can determine the approximate location of the arrhythmia focus. Because all of the point electrodes are placed against the cardiac tissue at the same time, better sensing capability is possible than with catheters with electrodes that are located entirely around the circumference of the catheter body. The tip electrode (16) may then be utilized in combination with an extracardiac electrode (not shown) in a unipolar mode to precisely locate the source of the arrhythmia focus. Once this source is determined, the tip electrode (16) is then utilized as an ablation electrode to ablate the arrhythmia focus. Alternatively, a separate ablation catheter may be utilized to ablate the arrhythmia focus.

By use of the catheter with pair of bipoles placed against the surface of the cardiac tissue, the distal portion of the appropriate catheter can be manipulated to the correct location within the heart. By precisely locating the catheter in the heart, there will be no dilution of the energy delivered due to the unfocused energy being dissipated over the entire cardiac chamber and lost in the circulating blood by a constantly moving tip of the ablating catheter. This permits a significantly reduced amount of energy to be applied during the ablation procedure. Further, time used to perform the procedure is significantly reduced over procedures where conventional electrodes are used. In addition, by this ablation procedure the same types of destruction of the discrete location can be achieved as have been accomplished, for example, in previous surgical procedures.

It will be apparent from the foregoing that while particular forms of the invention have been illustrated and described, various modifications can be made without departing from the spirit and scope of the invention. Accordingly, it is not intended that this invention be limited except as by the appended claims.

What is claimed is:

1. A catheter for sensing electrophysiological activity within a human heart comprising
an elongated catheter body having a distal end,
first and second point electrodes, which are secured in a surface of the elongated catheter body, comprising a first bipolar pair of electrodes, and
third and fourth point electrodes, which are secured in the surface of the catheter body, comprising a second bipolar pair of electrodes, wherein a line passing between the third and fourth point electrodes is within about 45 degrees of being perpendicular to a line passing through the first and second point electrodes and wherein each of the point electrodes is secured to a portion of the catheter body forming no more than about half of the circumference of the surface of the catheter body when viewed from the distal end of the catheter, such that all four electrodes can simultaneously be in contact with tissue of the human heart during a sensing procedure.

2. The catheter of claim 1 wherein the line passing between the third and fourth point electrodes is within about 30 degrees of being perpendicular to the line passing between the first and second point electrodes.

3. The catheter of claim 1 wherein the third point electrode is secured at a position on the catheter body which is more distal from the proximal end of the catheter body than is the fourth point electrode.

4. The catheter of claim 1 wherein the distance between the third and fourth point electrode is greater than the distance between the first and second point electrode.

5. The catheter of claim 1 wherein the third point electrode is secured on the catheter body at a position that is more distal from a proximal end of the catheter body than is the second point electrode.

6. The catheter of claim 1 wherein the fourth point electrode is secured on the catheter body at a position that is more proximal from a proximal end of the catheter body than is the second point electrode.

7. The catheter of claim 1 wherein the distance between the first and second point electrode is from about 0.1 mm. (0.004 inch) to about 4.0 mm. (0.16 inch).

8. The catheter of claim 1 further comprising a unipolar distal tip electrode secured to the distal end of the catheter body.

9. The catheter of claim 8 wherein the shortest distance between the unipolar distal tip electrode and the distal-most point electrode is from about 3.0 mm. (0.12 inch) to about 5.0 mm. (0.2 inch).

10. The catheter of claim 1 wherein the first and second point electrode bipoles are operably interfaced with conventional differential receiving and processing equipment to provide directional vectors to electrophysiological activity of the human heart.

11. The catheter of claim 10 further comprising one or more ring electrodes secured to the catheter body at a position proximal from the point electrodes.

12. The catheter of claim 1 wherein the point electrodes are formed in a circular, rectangular, square or non-regular shape.

13. A catheter for sensing electrophysiological activity within a human heart comprising an elongated catheter body having a distal end, first and second point electrodes, which are secured in a surface of the elongated catheter body, comprising a first bipolar pair of electrodes, and third and fourth point electrodes, which are secured in the surface of the catheter body, comprising a second bipolar pair of electrodes, wherein a line passing between the third and fourth point electrodes is within about 45 degrees of being perpendicular to a line passing through the first and second point electrodes wherein the first, second, third and fourth point electrodes are formed in a generally diamond-shaped configuration on the catheter body and wherein each of the point electrodes is secured to a portion of the catheter body forming no more than about half of the circumference of the surface of the catheter body when viewed from the distal end of the catheter, such that all four electrodes can simultaneously be in contact with tissue of the human heart during a sensing procedure.

14. A catheter for sensing electrophysiological activity within a human heart comprising an elongated catheter body having a distal end, a first and second point electrodes which are secured in a surface of the elongated catheter body comprising a first bipolar pair of electrodes, and a third point electrode which is secured in the surface of the elongated catheter body, wherein the third point electrode and the second point electrode comprise a second bipolar pair of electrodes and wherein each of the point electrodes is secured to a portion of the catheter body forming no more than about half of the circumference of the surface of the catheter body when viewed from the distal end of the catheter, such that all three electrodes can simultaneously be in contact with tissue of the human heart during a sensing procedure.

15. The catheter of claim 14 wherein the first point electrode is secured to the catheter body at a position more proximal from a proximal end of the catheter body than is the third point electrode.

16. The catheter of claim 15 wherein the second point electrode is secured to the catheter body at a position more proximal to a proximal end of the catheter than is the third point electrode.

17. The catheter of claim 14 wherein the distance between the first and second point electrodes is from about 0.1 mm. (0.004 inch) to about 4.0 mm. (0.16 inch).

18. The catheter of claim 17 wherein the distance between the third and second point electrode is greater than the distance between the first and second point electrode.

19. The catheter of claim 14 further comprising a unipolar distal tip electrode secured to the distal end of the catheter body.

20. The catheter of claim 19 wherein the shortest distance between the unipolar distal tip electrode and the distal-most point electrode is from about 3.0 mm. (0.12 inch) to about 5.0 mm. (0.2 inch).

21. The catheter of claim 14 wherein a line extending from the third point electrode through the second point electrode is within about 45 degrees of being perpendicular to the line passing between the first and second point electrodes.

22. The catheter of claim 14 wherein a line extending from the third point electrode through the second point electrode is within about 30 degrees of being perpendicular to the line passing between the first and second point electrodes.

23. A process for treatment of an arrhythmia focus within a human heart comprising introducing a sensing catheter within a chamber of the heart, wherein the catheter comprises a catheter body having a distal end, a first and second point electrodes, which are secured in a surface of the catheter body and comprise a first bipolar pair of electrodes, and third and fourth point electrodes, which are secured in the surface of the catheter body and comprise a second bipolar pair of electrodes, wherein a line passing between the third and fourth point electrodes is within about 45 degrees of being perpendicular to a line passing through the first and second point electrodes, wherein each of the point electrodes is secured to a portion of the catheter body forming no more than about half of the circumference of the surface of the catheter body when viewed from the distal end of the catheter body, such that all four electrodes can simultaneously be in contact with tissue of the human heart during a sensing procedure, and sensing the general direction within the heart from which activation waves of the arrhythmia focus are generated utilizing the catheter with the pair of bipolar pairs of electrodes.

* * * * *